United States Patent [19]

Lumma, Jr. et al.

[11] Patent Number: 4,966,967
[45] Date of Patent: Oct. 30, 1990

[54] 3,4,5,6-TETRAHYDRO-2H-1,7,4-BENZODIOXAZONINES AS CARDIOVASCULAR AGENTS

[75] Inventors: William C. Lumma, Jr., Pennsburg, Pa.; Gary B. Phillips, Wharton, N.J.

[73] Assignee: Berlex Laboratories, Inc., Cedar Knolls, N.J.

[21] Appl. No.: 408,023

[22] Filed: Sep. 15, 1989

[51] Int. Cl.$^5$ .................. C07D 413/00; C07D 413/04; C07D 498/00
[52] U.S. Cl. .................................... 540/568; 540/455; 548/336
[58] Field of Search ................ 540/468, 455; 514/183, 514/397, 449; 548/336

[56] References Cited

U.S. PATENT DOCUMENTS 4,208,410  6/1980  Rozsa et al. ..................... 540/468

OTHER PUBLICATIONS

Chemical Abstracts 82, 72957h, Benzocrown Ethers, Hogberg et al.

*Primary Examiner*—Mukund J. Shah
*Assistant Examiner*—Celia Chang
*Attorney, Agent, or Firm*—Elizabeth A. Bellamy; John L. White; I. William Millen

[57] ABSTRACT

This invention relates to novel 3,4,5,6-tetrahydro-2H-1,7,4-benzodioxazonines and their pharmaceutically acceptable salts. The compounds of the invention are cardiovascular agents and especially Class III antiarrhythmic agents.

15 Claims, No Drawings

3,4,5,6-TETRAHYDRO-2H-1,7,4-BENZODIOXAZONINES AS CARDIOVASCULAR AGENTS

FIELD OF INVENTION

This invention relates to novel 3,4,5,6-tetrahydro-2H-1,7,4-benzodioxazonines and their pharmaceutically acceptable salts. The compounds have demonstrated cardiovascular effects primarily antiarrhythmic in nature. Pharmaceutical compositions containing the compounds are proposed.

GENERAL DESCRIPTION OF THE INVENTION COMPOSITION-OF-MATTER ASPECT

In its composition-of-matter aspect this invention relates to 3,4,5,6-tetrahydro-2H-1,7,4-benzodioxazonines and their pharmaceutically acceptable salts.

Compounds encompassed by the invention are of the following Formula I:

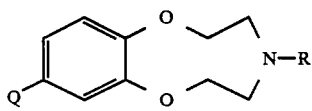

I wherein
Q is $CH_3SO_2NH$ or

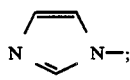

R is hydrogen, $C_1$-$C_8$ straight or branched chain alkyl, allyl, cycloalkyl, cycloalkylloweralkyl, phenylloweralkyl which may be substituted by up to three substituents selected from hydrogen, chlorine, bromine, fluorine, lower alkyl, and lower alkoxy or

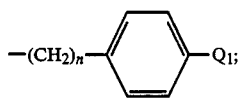

n is the integer 1,2,3 or 4;
$Q_1$ is $CH_3SO_2NH$ or

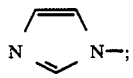

and the pharmaceutically acceptable salts thereof.

As used herein the term $C_1$-$C_8$ straight or branched chain alkyl shall be inclusive but not limited to such moieties as methyl, ethyl, propyl, isopropyl, butyl, isobutyl, tertiary butyl, sec. butyl, pentyl, isopentyl, hexyl, 3-methylpentyl, heptyl, 2-methylhexyl, octyl and 2-ethylhexyl. The term "lower" alkyl/alkoxy shall refer to a straight or branched chain of from 1 to 4 carbon atoms, for example, methyl, ethyl, propyl, isopropyl, butyl, isobutyl, tertiary butyl and sec. butyl. The term cycloalkyl shall refer to a saturated carbocyclic ring containing 3 to 6 carbon atoms whilst cycloalkylloweralkyl shall refer to said cycloalkyl at the terminus of a 1-4 straight carbon chain. Phenylloweralkyl shall refer to a phenyl at the terminus of a 1-4 straight carbon chain.

Also contemplated as part of this invention are the pharmaceutically acceptable salts of the compounds of Formula I. These are acid addition salts and may be formed with inorganic or organic acids. Illustrative but not restrictive examples of such acids include hydrochloric, hydrobromic, sulfuric, phosphoric, citric, acetic, propanoic, benzoic, naphthalenecarboxylic, oxalic, succinic, malic, maleic, adipic, lactic, tartaric, salicylic, methanesulfonic, 2-hydroxyethanesulfonic, toluenesulfonic, benzenesulfonic, camphorsulfonic and ethanesulfonic acids.

PROCESS ASPECT

The novel 3,4,5,6-tetrahydro-2H-1,7,4-benzodioxazonines of this invention are prepared by various processes and reactants known in the art. Such processes are illustrated, essentially, by the following scheme.

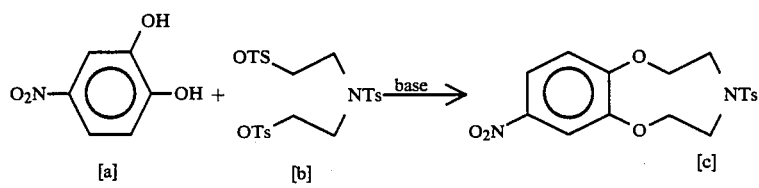

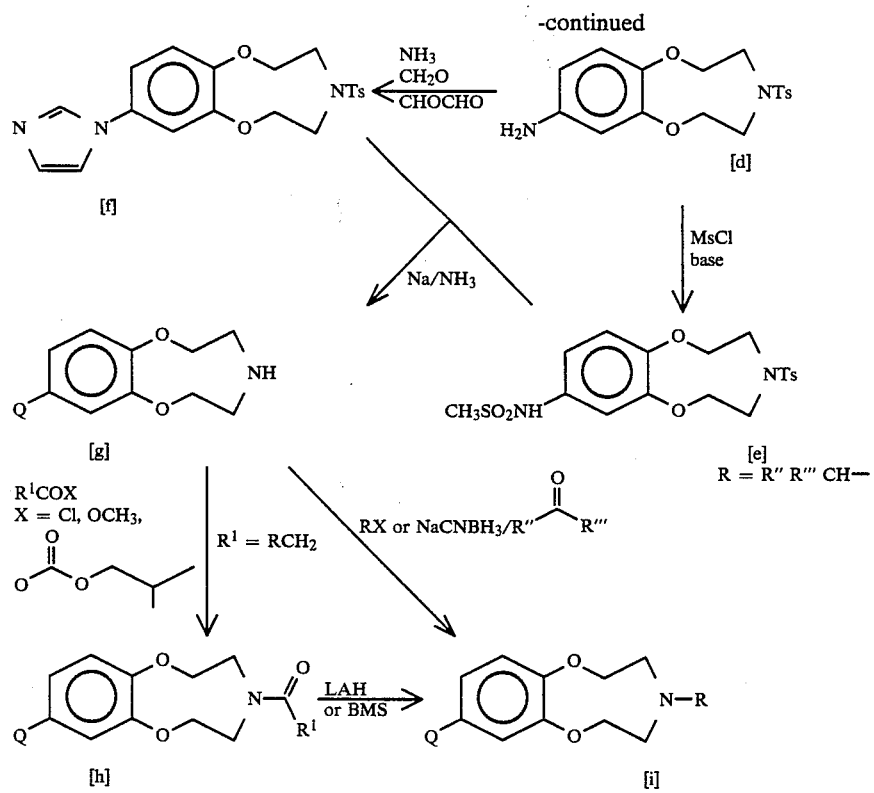

Combine 4-nitrocatechol [a] with 4-methyl-N,N-bis[2-[[(4-methylphenyl)sulfonyl]oxy]ethyl]benzenesulfonamide [b] in a suitable solvent (e.g. dimethylformamide, acetonitrile or dimethylsulfoxide) in the presence of a suitable base (e.g. K$_2$CO$_3$ or KOH) at a temperature of from about 50° to 150° C. to provide 1,4,7-benzodioxazonine [c]. Reduction of the compound [c] with stannous chloride in a solvent such as EtOH or EtOAc at a temperature of from between 30°-100° C. or with Pd(OH)$_2$ on carbon with hydrogen in a suitable solvent (e.g. methanol, ethanol, or ethyl acetate) provides the corresponding aniline [d].

Conversion of the aniline [d] to the various groups described in the invention are as follows. To obtain the imidazole [f] the aniline [d] is reacted with ammonium hydroxide, aqueous glyoxal, and aqueous formaldehyde in an appropriate solvent (e.g. ethanol or isopropanol) between 30°-100° C. To obtain the methanesulfonamide [e], the aniline is reacted with methanesulfonyl chloride or methanesulfonic anhydride in a solvent such as acetonitrile, propionitrile, or methylene chloride in the presence of a base such as K$_2$CO$_3$, triethylamine, or pyridine.

Removal of the toluenesulfonamide may be achieved by treatment of the compound [e or f] with sodium in liquid ammonia in the presence of some proton source such as methanol, tertbutyl alcohol, or ammonium chloride to obtain the secondary amine [g].

Conversion of the secondary amine [g] to the tertiary amine [i] may be carried out as follows. React the amine [g] with an excess of the appropriate alkyl halide in a suitable solvent (acetonitrile, dimethylformamide, or toluene) between 50°-100° C. to obtain the tertiary amine [i]. Alternatively react the secondary amine [g] with the appropriate carbonyl compound in the presence of NaCNBH$_3$ in a suitable solvent (methanol or ethanol) at a pH between 5-7 to obtain the tertiary amine [i]. Alternatively react the secondary amine [g] with the appropriate activated acid to provide [h]. The typical activated acids used are acid chlorides and mixed anhydrides. An alternate route to the amide [h] is to react the amine [g] with trimethyl-aluminum followed by the appropriate ester per Weinreb (Tetrahedron Lett. 1977, 4171). Reaction of the amide [h] with lithium aluminum hydride or borane dimethylsulfide complex in an etheral solvent at a temperature of between 20° and 100° C. provides the tertiary amine [i].

METHOD-OF-USE AND PHARMACEUTICAL COMPOSITION ASPECT

The 3,4,5,6-tetrahydro-2H-1,7,4-benzodioxazonines of this invention and their pharmaceutically acceptable salts as exemplified by Formula I are cardiovascular agents. As cardiovascular agents the compounds are primarily antiarrhythmic agents with Class III action. Certain of the compounds have also been found to have cardiotonic activity useful in the treatment of congestive heart failure. The utility as a cardiotonic agent may be determined by using isolated cat or ferret papillary muscle using standard isometric recording techniques. The compounds have been tested for their Class III activity via in vitro electrophysiologic testing utilizing standard intracellular microelectrode techniques in the canine cardiac Purkinje fiber.

In general the compounds of this invention may be administered orally or parenterally. The dosage administered will be dependent on the mammalian host being treated, the route of administration and the magnitude and type of cardiovascular effect to be elicited.

For oral administration the compound to be administered can be formulated by admixing with any number of suitable pharmaceutical diluents and carriers such as lactose, sucrose, starch powder, cellulose, calcium sulfate, sodium benzoate, and the like. Such formulations can be compressed into tablets or encapsulated into gelatin capsules for conventional oral administration.

For parenteral administration a compound of this invention can be formulated, for example, for intramuscular or intravenous administration. Such parenteral administration formulations can be accomplished with any of a number of pharmaceutically acceptable carriers and diluents to constitute an injectable liquid solution. Commonly used diluents and carriers include water or saline solutions, buffered aqueous solutions, including dispersing and surface active agents if necessary.

The invention described hereinabove is illustrated below in the Preparations and Examples, which, however, is not to be construed as limiting the scope of this invention.

PREPARATIONS

Preparation 1

4-[(4-Methylphenyl)sulfonyl]-9-nitro-3,4,5,6-tetrahydro-2H-1,7,4-benzodioxazonine To dimethylformamide (200 mL) add 4-nitrocatechol (13.8 g, 89 mmol), 4-methyl-N,N-bis[2-[[(4-methylphenyl)sulfonyl]oxy]ethyl]benzenesulfonamide (50.7 g, 89.4 mmol), and $K_2CO_3$ (27 g, 0.19 mol). Stir and heat the reaction at 110° C. Monitor the progress of the reaction by thin-layer chromatography. Upon completion remove the heat and add water (1.3 L) and methanol (300 mL). Collect the precipitate on paper by suction filtration. Wash the solid with water (2 L). Chromatograph the material on silica (300 g) with $CH_2Cl_2$ to obtain the title compound.

NMR ($CDCl_3$) $\delta = 2.41(s,3)$, 3.48(t,2), 3.55(t,2), 4.41(t,2), 4.67(t,2), 7.00(d,1), 7.25(d,2), 7.58(d,2), 7.86(s,1), 7.9(d,1) ppm.

Preparation 2

9-Amino-4-[(4-methylphenyl)sulfonyl]-3,4,5,6-tetrahydro-2H-1,7,4-benzodioxazonine To ethyl acetate (1 L) add 4-[(4-methylphenyl)sulfonyl]-9-nitro-3,4,5,6-tetrahydro-2H-1,7,4-benzodioxazonine (7.5 g, 20 mmol) and $Pd(OH)_2$ on carbon (1.0 g). Place the reaction mixture on a Parr hydrogenator and shake at 50 psi of hydrogen. Monitor the progress of the reaction by thin-layer chromatography. Upon completion remove the catalyst by suction filtration through celite. Remove the solvent in vacuo to obtain the title compound.

NMR ($CDCl_3$) $\delta = 2.4(s,3)$, 3.45(m,4), 3.6(s,2), 4.2(t,2), 4.4(t,2), 6.3(m,2), 6.8(d,1), 7.3(d,2), 7.65(d,2).

Preparation 3

4-[(4-Methylphenyl)sulfonyl]-9-[(4-methylsulfonyl)amino]-3,4,5,6-tetrahydro-2H-1,7,4-benzodioxazonine To methylene chloride (45 mL) add 9-amino-4-[(4-methylphenyl)sulfonyl]-3,4,5,6-tetrahydro-2H-1,7,4-benzodioxazonine (11.1 g, 32 mmol), pyridine (24 g, 0.31 mol), and methanesulfonyl chloride (4.1 g, 36 mmol). Monitor the progress of the reaction by thin-layer chromatography. Upon completion partition the reaction between 1M aqueous HCl and ethyl acetate. Wash the organic layer with 1M HCl and brine. Dry ($Na_2SO_4$) the organic layer and remove the solvent in vacuo to obtain the title compound.

NMR ($CDCl_3$) $\delta = 2.38(s,3)$, 2.95(s,3), 3.42(m,4), 4.35(m,4), 6.4(s,1), 6.8(m,2), 7.25(d,2), 7.6(d,2) ppm.

Preparation 4

9-(1H-Imidazol-1-yl)-4-[(4-methylphenyl)sulfonyl]-3,4,5,6-tetrahydro-2H-1,7,4-benzodioxazonine To reagent alcohol at 60° C. simultaneously add a solution of 9-amino-4-[(4-methylphenyl)sulfonyl]-3,4,5,6-tetrahydro-2H-1,7,4-benzodioxazonine and ammonium hydroxide diluted with alcohol and a solution of aqueous glyoxal and aqueous formaldehyde diluted to an equal volume with alcohol as the above solution. Monitor the progress of the reaction by thin-layer chromatography. Upon completion partition the reaction between ethyl acetate and aqueous $NaHCO_3$. Separate and dry the organic layer ($Na_2SO_4$). Remove the solvent in vacuo to obtain the title compound.

Preparation 5

9-[(Methylsulfonyl)amino]-4-[4-[(methylsulfonyl)amino]benzoyl]-3,4,5,6-tetrahydro-2H-1,7,4-benzodioxazonine To tetrahydrofuran add 9-[(methylsulfonyl)amino]-3,4,5,6-tetrahydro-2H-1,7,4-benzodioxazonine, pyridine, and 4-[(methylsulfonyl)amino]benzoyl chloride. Monitor the progress of the reaction by thin-layer chromatography. Upon completion, remove the solvent in vacuo. Partition the residue between aqueous $NaHCO_3$ and EtOAc. Separate the layers and wash the organic layer with 1M aqueous HCl. Separate and dry ($Na_2SO_4$) the organic layer. Remove the solvent in vacuo to obtain the title compound.

Preparation 6

4-(1H-Imidazol-1-yl)benzeneacetic acid, methyl ester

In a manner similar to preparation 4, react 4-aminobenzeneacetic acid, methyl ester with ammonium hydroxide, glyoxal, and formaldehyde to obtain the title compound.

NMR ($CDCl_3$) $\delta = 3.69(s,2)$, 3.72(s,3), 7.20(s,1), 7.25(s,1), 7.34(d,2), 7.40(d,2), 7.88(s,1) ppm.

Preparation 7

4-[2-[4-(1H-Imidazol-1-yl)phenyl]acetyl]-9-[(methylsulfonyl)amino]-3,4,5,6-tetrahydro-2H-1,7,4-benzodioxazonine To toluene add N-(3,4,5,6-tetrahydro-2H-1,7,4-benzodioxazonin-9-yl)methanesulfonamide, and trimethylaluminum at 0° C. Allow the reaction to warm to room temperature and add 4-(1H-imidazol-1-yl)acetic acid, methyl ester. Heat the reaction and monitor the progress by thin-layer chromatography. Upon completion make the solution basic with aqueous $NaHCO_3$ and extract with EtOAc. Remove the solvent in vacuo to obtain the title compound.

Preparation 8

4-[(Methylsulfonyl)amino]benzeneacetic acid, methyl ester

In a manner similar to preparation 3, react 4-aminobenzeneacetic acid, methyl ester with methanesulfonyl chloride, and pyridine to obtain the title compound.

NMR ($CDCl_3$) $\delta = 2.99(s,3)$, 3.61(s,2), 3.70(s,3), 7.10(s,1), 7.19(d,2), 7.25(d,2) ppm.

Preparation 9

9-(1H-Imidazol-1-yl)-4-[2-[4-[(methylsulfonyl)amino]-phenyl]acetyl]-3,4,5,6-tetrahydro-2H-1,7,4-benzodioxazonine In a manner similar to preparation 7, react 9-(1H-imidazol-1-yl)-3,4,5,6-tetrahydro-2H-1,7,4-benzodioxazonine, trimethylaluminum, and 4-[(methylsulfonyl)amino]benzeneacetic acid, methyl ester to obtain the title compound.

Preparation 10

9-(1H-Imidazol-1-yl)-4-[2-[4-(1H-imidazol-1-yl)phenyl]acetyl]-3,4,5,6-tetrahydro-2H-1,7,4-benzodioxazonine In a manner similar to preparation 7, react 9-(1H-imidazol-1-yl)-3,4,5,6-tetrahydro-2H-1,7,4-benzodioxazonine, trimethylaluminum, and 4-(1H-imidazol-1-yl)benzeneacetic acid, methyl ester to obtain the title compound.

Preparation 11

9-[(Methylsulfonyl)amino]-4-[2-[4-[(methylsulfonyl)amino]phenyl]acetyl]-3,4,5,6-tetrahydro-2H-1,7,4-benzodioxazonine In a manner similar to preparation 7, react 9-[(methylsulfonyl)amino]-3,4,5,6-tetrahydro-2H-1,7,4-benzodioxazonine, trimethylaluminum and 4-[(methylsulfonyl)amino]benzoic acid, methyl ester to obtain the title compound.

EXAMPLES

Example 1

N-(3,4,5,6-tetrahydro-2H-1,7,4-benzodioxazonin-9-yl)methanesulfonamide hydrochloride To ammonia (50 mL) and CH$_3$OH (9 mL) at −78° C. add 4-[(4-methylphenyl)sulfonyl]-9-[(methylsulfonyl)amino]-3,4,5,6-tetrahydro-2H-1,7,4-benzodioxazonine (8.5 g, 20 mmol) and sodium spheres (4.5 g, 0.20 mol). Monitor the progress of the reaction by thin-layer chromatography. Upon completion add ammonium chloride (11 g) and allow the reaction to warm to room temperature. Slurry the residue in ethyl acetate and remove the solid material by suction filtration through celite. Remove the solvent in vacuo. Dissolve the residue in CH$_3$OH and add methanolic hydrochloric acid. Remove the solvent in vacuo and recrystallize from acetonitrile to obtain the title compound.

NMR (DMSO-d$_6$, 80° C.) δ=2.94(s,3), 3.4(m,4), 4.33(dd,2), 4.42(dd,2), 6.89(dd,1), 6.95(d,1), 7.09(d,1), 9.4(br,3) ppm.

Example 2

N-(4-Propyl-3,4,5,6-tetrahydro-2H-1,7,4-benzodioxazonin-9-yl)methanesulfonamide, methanesulfonic acid salt To acetonitrile (200 mL) add N-(3,4,5,6-tetrahydro-2H-1,7,4-benzodioxazonin-9-yl)methanesulfonamide (2.9 g, 11 mmol) and iodopropane (17 g, 0.10 mol). Stir and heat the reaction at 55° C. Monitor the progress of the reaction by thin-layer chromatography. Upon completion remove the solvent in vacuo. Partition the residue between CH$_2$Cl$_2$ and sat. NaHCO$_3$. Separate and dry the organic layer with Na$_2$SO$_4$. Remove the solvent in vacuo. Flash chromatograph the residue on silica (90 g) with CH$_2$Cl$_2$/CH$_3$OH (19/1). The resulting material is dissolved in CH$_3$OH (5 mL) and methanesulfonic acid (0.95 g, 9.9 mmol). Remove the solvent in vacuo and recrystallize the residue from isopropanol to obtain the title compound.

NMR (DMSO-d$_6$) δ=0.94(t,3), 1.8(m,2), 2.35(s,3), 3.00(s,3), 3.2(m,2), 3.6(m,4), 4.4(m,2), 4.5(m,2), 6.9(m,2), 7.15(d,1), 9.7(br,1), 9.76(s,1) ppm.

Example 3

N-(4-Ethyl-3,4,5,6-tetrahydro-2H-1,7,4-benzodioxazonin-9-yl)methanesulfonamide methanesulfonic acid salt In a manner similar to example 2 react N-(3,4,5,6-tetrahydro-2H-1,7,4-benzodioxazonin-9-yl)methanesulfonamide with iodoethane to obtain the title compound.

NMR (DMSO-d$_6$) δ=1.29(t,3), 2.32(s,3), 2.98(s,3), 3.24–3.72(m,6), 4.38(m,2), 4.47(t,2), 6.90–7.0(m,2), 7.12(d,1), 9.84(br,1), 9.74(s,1).

Example 4

N-(4-Cyclopentyl-3,4,5,6-tetrahydro-2H-1,7,4-benzodioxazonin-9-yl)methanesulfonamide To methanol add N-(3,4,5,6-tetrahydro-2H-1,7,4-benzodioxazonin-9-yl)methanesulfonamide, cyclopentanone, and NaBH$_3$CN. Adjust the pH to six with concentrated HCl. Monitor the progress of the reaction by thin-layer chromatography. Upon completion add concentrated HCl until gas evolution ceases. Partition the reaction mixture between EtOAc and water. Add 1N aqueous NaOH until the solution is basic. Separate and dry the organic layer over Na$_2$SO$_4$. Filter the drying agent and remove the solvent in vacuo to obtain the title compound.

Example 5

9-(1H-Imidazol-1-yl)-3,4,5,6-tetrahydro-2H-1,7,4-benzodioxazonine

In a manner similar to example 1 react 9-(1H-imidazol-1-yl)-4-[(4-methylphenyl)sulfonyl]-3,4,5,6-tetrahydro-2H-1,7,4-benzodioxazonine with sodium in methanol and ammonia to obtain the title compound.

Example 6

4-(2-Cyclohexylethyl)-9-(1H-imidazol-1-yl)-3,4,5,6-tetrahydro-2H-1,7,4-benzodioxazonine In a manner similar to example 4, react 9-(1H-imidazol-1-yl)-3,4,5,6-tetrahydro-2H-1,7,4-benzodioxazonine with cyclohexaneacetaldehyde and NaBH$_3$CN to obtain the title compound.

Example 7

N-[4-(Cyclopropylmethyl)-3,4,5,6-tetrahydro-2H-1,7,4-benzodioxazonin-9-yl]methanesulfonamide In a manner similar to example 4, react N-(3,4,5,6-tetrahydro-2H-1,7,4-benzodioxazonin-9-yl)methanesulfonamide with cyclopropanecarboxaldehyde and NaBH$_3$CN to obtain the title compound.

Example 8

N-[4-[[4-[(Methylsulfonyl)amino]phenyl]methyl]-3,4,5,6-tetrahydro-2H-1,7,4-benzodioxazonin-9-yl]methanesulfonamide To tetrahydrofuran add 9-[(methylsulfonyl)amino]-4-[4-(methylsulfonyl)amino]benzoyl]-3,4,5,6-tetrahydro-2H-1,7,4-benzodioxazonine and lithium aluminum hydride. Reflux the reaction mixture. Monitor the progress of the reaction by thin-layer chromatography. Upon completion add water and 2N aqueous NaOH to precipitate the salts. Suction filter the material through celite. Remove the solvent in vacuo to obtain the title compound.

Example 9

N-[4-[2-[4-(1H-Imidazol-1-yl)]ethyl]-3,4,5,6-tetrahydro-2H-1,7,4-benzodioxazonin-9-yl]methanesulfonamide In a manner similar to example 8, react 4-[2-[4-(1H-imidazol-1-yl)phenyl]acetyl]-9-[(methylsulfonyl)amino]-3,4,5,6-tetrahydro-2H-1,7,4-benzodioxazonine with lithium aluminum hydride to obtain the title compound.

Example 10

N-[4-[2-[9-(1H-Imidazol-1-yl)-3,4,5,6-tetrahydro-2H-1,7,4-benzodioxazonin-4-yl]ethyl]phenyl]methanesulfonamide In a manner similar to example 8, react 9-(1H-imidazol-1-yl)-4-[2-[4-[(methylsulfonyl)amino]phenyl]acetyl]-3,4,5,6-tetrahydro-2H-1,7,4-benzodioxazonine with lithium aluminum hydride to obtain the title compound.

Example 11

9-(1H-Imidazol-1-yl)-4-[2-[4-(1H-imidazol-1-yl)phenyl]ethyl]-3,4,5,6-tetrahydro-2H-1,7,4-benzodioxazonine In a manner similar to example 8, react 9-(1H-imidazol-1-yl)-4-[2-[4-(1H-imidazol-1-yl)phenyl]acetyl]-3,4,5,6-tetrahydro-2H-1,7,4-benzodioxazonine with lithium aluminum hydride to obtain the title compound.

Example 12

N-[4-[2-(3,4,5-Trimethoxyphenyl)ethyl]-3,4,5,6-tetrahydro-2H-1,7,4-benzodioxazonin-9-yl]methanesulfonamide In a manner similar to example 4, react N-(3,4,5,6-tetrahydro-2H-1,7,4-benzodioxazonin-9-yl)methanesulfonamide, 3,4,5-trimethoxybenzeneacetaldehyde, and NaBH$_3$CN to obtain the title compound.

Example 13

N-[4-[2-[4-[(Methylsulfonyl)amino]phenyl]ethyl]-3,4,5,6-tetrahydro-2H-1,7,4-benzodioxazonin-9-yl]methanesulfonamide In a manner similar to example 8, react 9-[(methylsulfonyl)amino]-4-[2-[4-[(methylsulfonyl)amino]phenyl]acetyl]-3,4,5,6-tetrahydro-2H-1,7,4-benzodioxazonine with lithium aluminum hydride to obtain the title compound.

It is comtemplated that when Q or Q$_1$ are NO$_2$ and R and n are as in Formula I, the compounds would have similar cardiovascular effects.

We claim:
1. A compound of the following Formula I

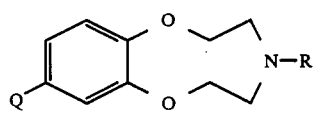

wherein
Q is CH$_3$SO$_2$NH— or

R is hydrogen, C$_1$-C$_8$ straight or branched chain alkyl, allyl, cycloalkyl, cycloalkylloweralkyl, phenylloweralkyl which may be substituted by up to three substituents selected from hydrogen, chlorine, bromine, fluorine, loweralkyl and loweralkoxy or

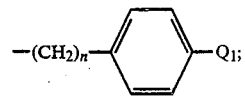

n is the integer 1,2,3 or 4 and Q$_1$ is CH$_3$SO$_2$NH— or

and the pharmaceutically acceptable salts thereof.
2. A compound of claim 1 where Q is CH$_3$SO$_2$NH—.
3. A compound of claim 1 where Q is

4. A compound of claim 2 which is N-(3,4,5,6-tetrahydro-2H-1,7,4-benzodioxazonin-9-yl)methanesulfonamide.
5. A compound of claim 2 which is N-(4-propyl-3,4,5,6-tetrahydro-2H-1,7,4-benzodioxazonin-9-yl)methanesulfonamide.
6. A compound of claim 2 which is N-(4-ethyl-3,4,5,6-tetrahydro-2H-1,7,4-benzodioxazonin-9-yl)methanesulfonamide.
7. A compound of claim 2 which is N-(4-cyclopentyl-3,4,5,6-tetrahydro-2H-1,7,4-benzodioxazonin-9-yl)methanesulfonamide.
8. A compound of claim 2 which is N-[4-(cyclopropylmethyl)-3,4,5,6-tetrahydro-2H-1,7,4-benzodioxazonin-9-yl]methanesulfonamide.
9. A compound of claim 2 which is N-[4-[[4-[(methylsulfonyl)amino]phenyl]methyl]-3,4,5,6-tetrahydro-2H-1,7,4-benzodioxazonin-9-yl]methanesulfonamide.
10. A compound of claim 2 which is N-[4-[2-[4-(1H-imidazol-1-yl)]phenyl]ethyl]-3,4,5,6-tetrahydro-2H-1,7,4-benzodioxazonin-9-yl]methanesulfonamide.
11. A compound of claim 2 which is N-[4-[2-(3,4,5-trimethoxyphenyl)ethyl]-3,4,5,6-tetrahydro-2H-1,7,4-benzodioxazonin-9-yl]methanesulfonamide.
12. A compound of claim 2 which is N-[4-[2-[4-[(methylsulfonyl)amino]phenyl]ethyl]-3,4,5,6-tetrahydro-2H-1,7,4-benzodioxazonin-9-yl]methanesulfonamide.
13. A compound of claim 3 which is 9-(1H-imidazol-1-yl)-3,4,5,6-tetrahydro-2H-1,7,4-benzodioxazonine.
14. A compound of claim 3 which is 4-(2-cyclohexylethyl)-9-(1H-imidazol-1-yl)-3,4,5,6-tetrahydro-2H-1,7,4-benzodioxazonine.
15. A compound of claim 3 which is N-[4-[2-[9-(1H-imidazol-1-yl)-3,4,5,6-tetrahydro-2H-1,7,4-benzodioxazonin-4-yl]ethyl]phenyl]methanesulfonamide.

* * * * *